United States Patent
Lyons et al.

(10) Patent No.: US 10,835,629 B2
(45) Date of Patent: Nov. 17, 2020

(54) SINGLET OXYGEN GENERATING DEVICE FOR SELECTIVE DESTRUCTION OF PATHOGENS

(71) Applicants: Research Foundation of the City University of New York, New York, NY (US); SingletO2 Therapeutics LLC, New Providence, NJ (US)

(72) Inventors: Alan M. Lyons, New Providence, NJ (US); Alexander Greer, New York, NY (US); QianFeng Xu, Staten Island, NY (US)

(73) Assignee: Research Foundation of the City University of New York, New York, NY (US)

( * ) Notice: Subject to any disclaimer, the term of this patent is extended or adjusted under 35 U.S.C. 154(b) by 507 days.

(21) Appl. No.: 15/729,005

(22) Filed: Oct. 10, 2017

(65) Prior Publication Data
US 2018/0099063 A1  Apr. 12, 2018

Related U.S. Application Data

(60) Provisional application No. 62/405,583, filed on Oct. 7, 2016.

(51) Int. Cl.
*A61L 2/26* (2006.01)
*A61C 17/02* (2006.01)
(Continued)

(52) U.S. Cl.
CPC ............... *A61L 2/26* (2013.01); *A61C 3/005* (2013.01); *A61C 17/02* (2013.01);
(Continued)

(58) Field of Classification Search
CPC ... A61L 2/26; A61L 2/202; A61L 2/20; A61C 3/005; A61C 17/02; A61C 17/0202;
(Continued)

(56) References Cited

U.S. PATENT DOCUMENTS

| 8,450,359 B2 | 5/2013 | McCoy et al. |
| 2008/0255498 A1* | 10/2008 | Houle .................... A61C 17/02 604/20 |

(Continued)

FOREIGN PATENT DOCUMENTS

WO   WO0110327   2/2001

OTHER PUBLICATIONS

Bartusik, D. et al.; Bacterial Inactivation by a Singlet Oxygen Bubbler: Identifying Factors Controlling the Toxicity of 1O2 Bubbles; Environmental Science & Technology; Oct. 18, 2012; pp. 12098-12104; vol. 46; ACS Publications.

(Continued)

*Primary Examiner* — Nicholas D Lucchesi
(74) *Attorney, Agent, or Firm* — Peter J. Mikesell; Schmeiser, Olsen & Watts, LLP (57) ABSTRACT

A device for generating singlet oxygen is provided. The device has elongated posts extending from a surface, the lateral sides of which have particles with a sensitizer that converts triplet oxygen to single oxygen upon exposure to light. An optical fiber conveys light to the sensitizer and a gas supply tube conveys oxygen to the sensitizer. The device is configured to keep the sensitizer from contacting external fluids, such as saliva.

20 Claims, 11 Drawing Sheets

(51) Int. Cl.
*A61L 2/20* (2006.01)
*A61C 3/00* (2006.01)
*C01B 13/02* (2006.01)
*A61C 8/02* (2006.01)
*A61C 19/04* (2006.01)

(52) U.S. Cl.
CPC .......... *A61C 17/0202* (2013.01); *A61L 2/202* (2013.01); *A61C 8/0006* (2013.01); *A61C 19/043* (2013.01); *A61L 2/20* (2013.01); *C01B 13/02* (2013.01); *C01B 13/0203* (2013.01)

(58) Field of Classification Search
CPC ..... A61C 8/0006; A61C 19/043; C01B 13/02; C01B 13/0203
See application file for complete search history.

(56) References Cited

U.S. PATENT DOCUMENTS

| | | | |
|---|---|---|---|
| 2009/0012587 | A1 | 1/2009 | Wang et al. |
| 2009/0043065 | A1* | 2/2009 | Khabashesku ......... B01J 19/127 526/347.1 |
| 2012/0245506 | A1* | 9/2012 | Piergallini ......... A61K 31/4166 604/20 |
| 2013/0123642 | A1* | 5/2013 | Yamaguchi ......... A61N 5/0601 600/476 |
| 2018/0099063 | A1* | 4/2018 | Lyons ................ A61C 17/02 |

OTHER PUBLICATIONS

Bartusik, D. et al.; Generating Singlet Oxygen Bubbles: A New Mechanism for Gas-Liquid Oxidations in Water; Langmuir, Jan. 20, 2012; pp. 3053-3060; vol. 28; ACS Publications.

Aebisher, D. et al.; Superhydrophobic Photosensitizers. Mechanistic Studies of 1O2 Generation in the Plastron and Solid/Liquid Droplet Interface; JACS; Dec. 2, 2013; pp. 18990-18998; vol. 135; ACS Publications.

Zhao, Y. et al.; Singlet Oxygen Generation on Porous Superhydrophobic Surfaces: Effect of Gas Flow and Sensitizer Wetting on Trapping Efficiency; The Journal of Physical Chemistry; Jun. 2, 2014; pp. 10364-10371; vol. 118; ACS Publications.

* cited by examiner

SINGLET OXYGEN GENERATING DEVICE FOR SELECTIVE DESTRUCTION OF PATHOGENS

CROSS-REFERENCE TO RELATED APPLICATIONS

This application claims priority to and is a non-provisional of U.S. Patent Application 62/405,583 (filed Oct. 7, 2016), the entirety of which is incorporated herein by reference.

BACKGROUND OF THE INVENTION

The subject matter disclosed herein relates to the use of singlet oxygen to kill cells such as pathogens, bacteria and/or cancer cells. Pathogens and undesirable tissues (e.g. cancer cells) pose a significant risk to human health. A variety of treatment methods are available to destroy these pathogens but none has proven to be entirely successful. Often the cytotoxicity of the treatment agent inappropriately destroys surrounding tissue or is otherwise not sufficiently selective or the treatment agent is persistent thereby allowing pathogens to develop resistance to the agent. An improved method for the selective destruction of pathogens is therefore desirable. The discussion above is merely provided for general background information and is not intended to be used as an aid in determining the scope of the claimed subject matter.

BRIEF DESCRIPTION OF THE INVENTION

A device for generating singlet oxygen is provided. The device has elongated posts extending from a surface, the lateral sides of which have particles with a sensitizer that converts triplet oxygen to single oxygen upon exposure to light. An optical fiber conveys light to the sensitizer and a gas supply tube conveys oxygen to the sensitizer. The device is configured to keep the sensitizer from contacting external fluids, such as saliva.

In a first embodiment, a device for generating singlet oxygen is provided. The device comprises a hand-piece comprising a conical tip at a terminus of the hand-piece; a gas supply tube that conveys oxygen to the conical tip; an optical fiber that conveys light to the conical tip. The conical tip is detachable from the hand-piece and comprises: a cylindrical substrate with an internal surface that is at least partially coated with particles that comprise a sensitizer, wherein the sensitizer converts triplet oxygen to singlet oxygen upon exposure to light; the optical fiber conveys light to the sensitizer; the gas supply tube is disposed upstream of the sensitizer such that oxygen is conveyed to the sensitizer; at least one opening disposed downstream of the sensitizer that directs singlet oxygen to a treatment site; and a hydrophobic barrier that separates the sensitizer particles from the opening, thereby protecting the sensitizer from contacting an external fluid.

In a second embodiment, a method for treating a periodontal pocket of a patient with singlet oxygen is provided. The method comprises conveying a gas comprising triplet oxygen through a hand-piece, the hand-piece comprising a conical tip at a terminus of the hand-piece; a gas supply tube that conveys oxygen to the conical tip; an optical fiber that conveys light to the conical tip. The conical tip is detachable from the hand-piece and comprises a cylindrical substrate with an internal surface that is at least partially coated with particles that comprise a sensitizer, wherein the sensitizer converts the triplet oxygen to singlet oxygen upon exposure to light; the optical fiber conveys light to the sensitizer; the gas supply tube is disposed upstream of the sensitizer such that oxygen is conveyed to the sensitizer; at least one opening disposed downstream of the sensitizer that directs singlet oxygen to a treatment site; a hydrophobic barrier that separates the sensitizer particles from the opening, thereby protecting the sensitizer from contacting an external fluid. The method further comprises inserting the opening of the conical tip into the periodontal pocket of the patient such that the opening is proximate the treatment site; actuating a light source that provides light to the optical fiber, thereby converting the triplet oxygen to the singlet oxygen using the sensitizer; and permitting the singlet oxygen to flow from the sensitizer to the opening and then to the treatment site, thereby treating the periodontal pocket of the patient with the singlet oxygen.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 8C depicts one method for producing elongated ridges onto a substrate while

DETAILED DESCRIPTION OF THE INVENTION

Periodontal infections continue to plague the world's population primarily due to inadequate dental care, increasing rates of diabetes, and tobacco use. Scaling and Root Planing (S&RP) with or without antibiotics suffers from bacterial resistance and recurrent infections. Periowave, a photodynamic therapy (PDT) method has been used, but there is difficulty in treating deep in pockets, requiring multiple visits. Thus, there is a need for treatment strategies that can generate singlet oxygen site-specifically for enhanced bacterial destruction in deep periodontal pockets (up to 10 mm) to combat recurrence. The disclosed superhydrophobic PDT approach is significant because it could be used as a sole therapy or simultaneously with S&RP to reduce or eliminate these problems.

The disclosed device generates singlet oxygen to eradicate bacterial biofilms in pockets 1-10 mm deep during a single visit rather than multiple visits. The system has at least one of the following advantages: (i) singlet oxygen delivery to periodontal pockets where the superhydrophobic surface provides a barrier so the sensitizer does not contact tissue, (ii) precision for limiting near-neighbor effects where bacterial pockets are adjacent to healthy gum tissue, (iii) countering bacteria hypoxia by delivery of oxygen concentrations by the device tip that are sufficient to sustain PDT, and (iv) combining singlet oxygen disinfection with simultaneous photobiomodulation to stimulate healing and relief from inflammation. For a sensitizer to generate singlet oxygen the sensitizer should strongly absorb light. If the periodontal pocket is deep, the tissue can absorb a portion of the light. The disclosed device addresses this concern. Deep periodontal pockets also have little oxygen present. The disclosed device addresses this concern. The lifetime of singlet oxygen is also known to be shorter in liquid environments than in gaseous environments. The disclosed device enhances the time singlet oxygen spends in the gas phase and thus permits deeper tissue penetration. In other embodiments, the device may be used for non-periodontal treatments such as tumor eradiction and bacterial killing in stagnating wounds.

Figure 1:
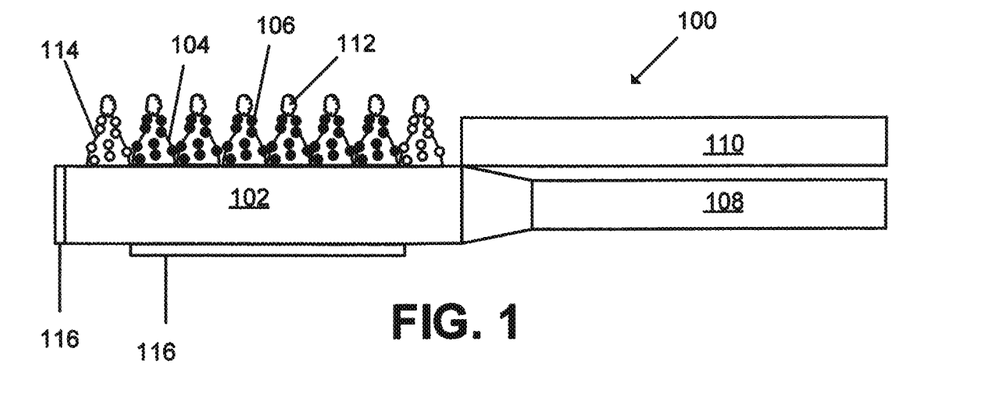
FIG. 1 is a bisected profile view of an assembly for producing singlet oxygen.
Figure 2:
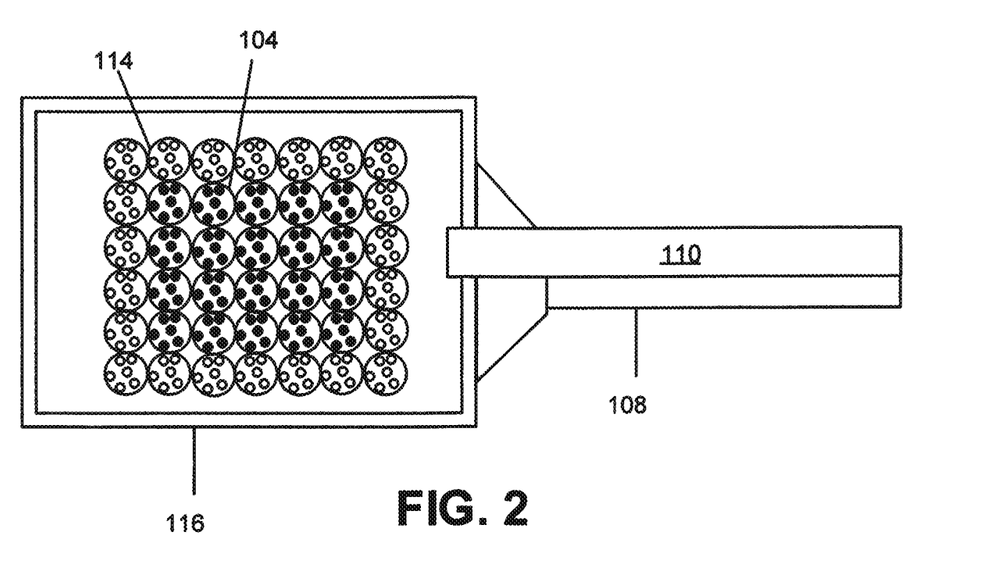
FIG. 2 is a top view of the assembly of FIG. 1.

FIG. 1 depicts an assembly 100 that comprises a substrate 102 with a plurality of elongated posts 104 mounted on a surface thereof. The substrate may be a thin, transparent substrate such a glass, polydimethylsiloxane (PDMS), polymethyl methacrylate (PMMA) or polyethylene terephthalate (PET). In one embodiment, the thickness is between 25 microns and 2 mm. In another embodiment, the thickness is between 25 microns and 500 microns. In yet another embodiment, the thickness is between 25 microns and 250 microns. Each elongated post 104 has sensitizers 106 disposed on at least an external surface of the elongated post 104. The sensitizer is disposed on a lateral surface of the elongated post 104 to prevent external fluids from contacting the sensitizer. The sensitizers 106 generate single oxygen ($^1O_2$) from triplet oxygen ($^3O_2$) upon photoactivation. Such sensitizers are known to those skilled in the art. Examples include porphyrins, phthalocyanines (e.g. Si-phthalocyanine), fullerenes, chlorins, bacteriochlorins, temoporfin (e.g. FOSCAN®) and BODIPY compounds, xanthene and fluorscein dyes (e.g., rose bengal), phenothiazines (e.g., methylene blue), cyanine dyes bearing polymethine chains (e.g., indocyanine green), imides (e.g., naphthalene diimide), polycyclic aromatic hydrocarbons (e.g., naphthalene, anthracene), carbonyl compounds (e.g., benzophenone, fluorenone), nitrogen heterocycles (e.g., acridine, phenazine), sulfur heterocycles (e.g., alpha-terthienyl), coordination compounds (e.g., $Ru(bpy)_3Cl_2$). There are well-known routes to binding sensitizer to glass. Photoactivation may be accomplished through optical fiber 108 which routes light from a light source to the optically transparent substrate and to the sensitizer particles. Mirrors 116, for example, can be used to enhance coupling of light between the substrate 102 and the sensitizer particles. Oxygen can be introduced to the elongated posts 104 using gas supply tube 110. In one embodiment, oxygen is supplied along with an inert gas such as nitrogen or argon. The use of sensitizers on particles disposed on the lateral side of elongated posts provides high surface area contact with gas flow while also providing uniform illumination. For some embodiments, it is desirable to keep the sensitizers 106 away from fluid, such as saliva or other biological fluids. In the embodiment of FIG. 1, this is accomplished by applying inert particles 112 (i.e. sensitizer-free particles) to the top of each elongated post 104. Examples of suitable inert particles include hydrophobic particles, such as silane-treated or Polydimethylsiloxane (PDMS)-treated silica (e.g. CAB-O-SIL®) or polytetrafluoroethylene (PTFE) particles or a food-grade fumed silica (e.g. AEROSIL® 380 F manufactured by Evonik). Additionally, the embodiment of FIG. 1 includes guard posts 114 that circumscribe the elongated posts 104. Elongated posts 104 comprise sensitizers while guard posts 114 comprise inert hydrophobic particles. FIG. 2 provides a top view of the embodiment of FIG. 1 and more clearly illustrates the use of the guard posts 114 to circumscribe the plurality of elongated posts 104. The guard posts 114 repel liquids and thereby protect the elongated posts 104 from such liquids. The guard posts 114 also protect the patient by preventing bodily fluids from contacting the sensitizer. In FIG. 1 and FIG. 2, a mirror 116 is provided to reflect light and enhance the photoactivation of the sensitizer.

The particles serve to increase the surface area of the sensitizer exposed to oxygen. The particles should be small so that the surface area is enhanced. For example, AEROSIL® 380 has a specific surface area of 380 $m^2$ per g with primary particle size of 7 nm. The higher the surface area, the more sensitizer can be loaded and remain available on the surface of the particle to contact both oxygen and light. Alternatively, the particles could be larger, such as 100 nm, 1000 nm (1 micron), 10 microns or 100 microns in diameter. In one embodiment, the particles have a diameter between 10 microns and 100 microns. The larger particles may be advantageous to avoid restrictions due to the use of nanoparticles in contact with human tissue.

The particles can be solid or porous. In some embodiments, porous particles with nanometer or micrometer dimensions are used to further increase the available surface area for sensitizer attachment while persevering the ability of oxygen to diffuse into and out of the particles. Typical porous glass has a specific surface from 10 to 300 m² per g. By regulating the manufacturing parameters, a porous glass with a pore size of between 0.4 and 1000 nm is produced.

Particles can be made using a sol-gel process where the sensitizer is combined with a glass forming composition (e.g. sol-gel) such that the sensitizer is dispersed throughout the glass. This sol-gel containing a sensitizer can then be ground to a fine power (particle sizes less than 100 microns) and partially embedded into the elongated posts. In one embodiment, the sol-gel is formed such that it becomes porous so that oxygen can diffuse into and out of the micron or nm sized particles and thereby take advantage of sensitizer molecules located both on the surface of the particle as well as the interior of the particle. In one embodiment, the particles consist of the sensitizer.

The particles can be treated to be hydrophobic or hydrophilic. Hydrophobic particles have the advantage that water and bodily fluids are repelled to minimize or prevent liquid-fluid contact. Hydrophobicity can be achieved by several techniques including the use of PDMS, silanes, as well as fluorinating agents (e.g. fluorosilanes).

Synthetic methods can be used to covalently attach sensitizers to native and fluorinated silica particles. For example, a chlorin trimethyl ester can be bound by its ester groups to the OH groups of partially fluorinated silica. Other sensitizer substituents that could be used to bond to silica include halogens, alcohols, carboxylic acids, tosylates, and borates. Nucleophilic substitution chemistry can be used. Other coupling reactions can also be used such as dehydrative carbodiimide "EDC" coupling, NaH chemistry, Sonogashira coupling, Suzuki coupling, click chemistry (e.g., azide-alkyne Huisgen cycloaddition), alkene additions, etc. The sensitizers can also be adsorbed non-covalently over a native silica surface. Sensitizer loading is done to maximize singlet oxygen output.

For example, silica particles (0.4 g) may be soaked in 0.6 M 3,3,4,4,5,5,6,6,6-nonafluorohexyltrimethoxysilane and refluxed in toluene (30 mL) for 24 h, which leads to the replacement of the SiOH groups for the fluorosilane C—H and C—F groups. Any nonafluorohexyltrimethoxysilane that is not covalently attached to the silica surface is washed away by Soxhlet extraction in methanol for 24 h.

A specific example to covalently attach sensitizers to fluorinated silica particles is as follows: chlorin $e_6$ trimethyl ester (0.05 mmol) is reacted with 3-iodopropyltrimethoxysilane (0.25 mmol) and NaH (0.01 mmol) in 5 mL dry THF, and refluxing the mixture at 70° C. for 24 h. The THF is evaporated and leave a residue of chlorin-silane, which is added to 50 mL toluene and 0.4 g silica, and refluxed at 110° C. for 24 h. Chlorin-silane is loaded in 0.17 mmol amounts (99.5% of the SiOH groups) onto silica.

Figure 3:
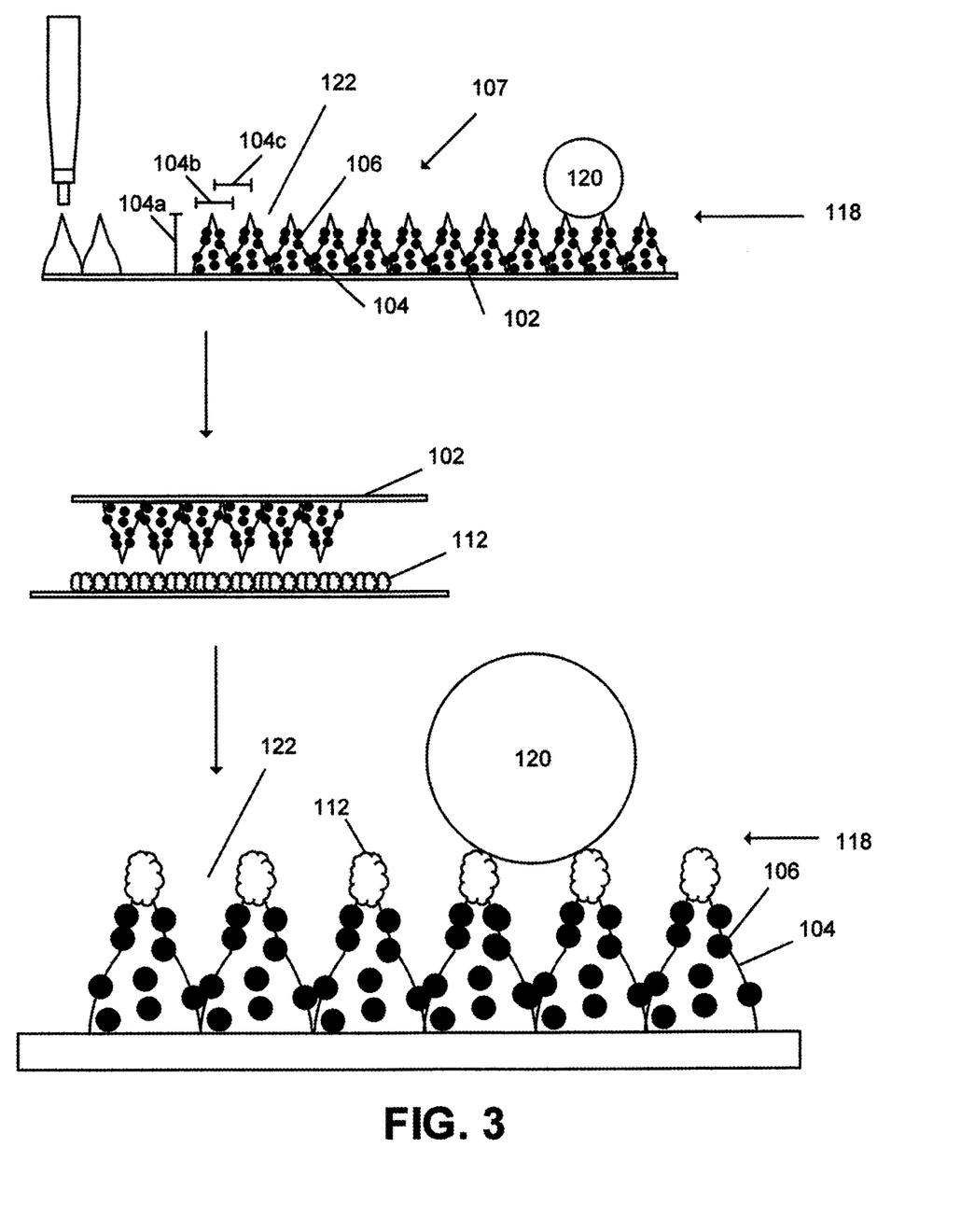
FIG. 3 depicts one method for printing elongated posts onto a substrate.

The elongated posts 104 and the guard posts 114 can be formed using conventional methods such as printing, three-dimensional (3D) printing, molding, and the like. In the embodiment of FIG. 3, a robotic dispensing system is used to print PDMS arrays. Particles (e.g. silica nanoparticles) can be functionalized with the sensitizer and subsequently coated uniformly over the surface of the elongated posts 104. For example, when printing elongated posts using a room temperature vulcanizing (RTC) silicone resin, the elongated posts remain soft and tacky after printing. Particles containing the sensitizer are poured onto this soft, tacky surface such that the post surfaces are at least partially coated. The elongated posts are then cured (either the posts are cured at room temperature for several hours, or the posts are cured at elevated temperature for less time, e.g. 65° C. for 30 minutes). After cure, excess particles are removed by rotating the surface upside down. Blowing clean, dry gas (e.g. air or nitrogen) over the surface further ensures that all particles not bonded to the elongated posts are removed. Another approach would be to dip the elongated post substrate into a bed of the particles. A fluidized bed enables good contact without exerting forces on the uncured elongated posts that could distort their shape. The particles can be located so that they cannot come into direct contact with biofluids and/or tissue. The safety of some sensitizers is not known and so it may be desirable to avoid contact with biological tissue.

The elongated posts 104 have a length 104a, a base width 104b and a pitch 104c. In one embodiment, each elongated post has a base diameter of about 400 microns and taper to a tip diameter of a few microns, a pitch of 500 microns and a height of 900 microns. In one embodiment, the elongated posts are printed on a square array, but could equally well be printed on a hexagonal array, or a circular array—or even a stochastic distribution. Instead of parallel posts, other features could be used as well, for example a series of parallel ridges. The pitch 104c, combined with the surface irregularities from particles 106 produce a hydrophobic barrier 118 in the form of a superhydrophobic surface. A superhydrophobic surface is that surface that exhibit a contact angle of at least 140° (or 150°) with water when tested in accordance with ASTM D7334 08(2013). An opening 122 permits singlet oxygen to escape. The gas supply tube 110 is disposed upstream of the sensitizer 106 while the opening 122 is disposed downstream of the sensitizer 106. This facilitates the rapid flow of singlet oxygen out of the opening 122 to take advantage of the longer lifetime of singlet oxygen in the gas phase. In one embodiment, the base width 104b is between 300 microns and 500 microns, the pitch is between 400 microns and 600 microns (but is greater than the base width 104b) and the length is between 800 microns and 1000 microns. The tip diameter is between 1 micron and 5 microns.

As shown in FIG. 3, elongated posts 104 may be printed into a surface. The elongated posts 104 may be formed of a polymeric material (e.g. polydimethysiloxane, PDMS) or other suitable material. Other suitable materials include epoxy resins, polyurethane resins, polyester resins, phenol-formaldehyde resins, poly(methyl methacrylate) resins, etc. The elongated posts 104 are then coated with particles comprising the sensitizer 106 to produce assembly 107 which may be used to generate singlet oxygen as described elsewhere in this specification. In another embodiment, after the polymeric material is cured the tips of the elongated posts 104 can be treated with inert particles 112 (e.g. unfunctionalized $SiO_2$ particles). The inert particles 112 further increase the hydrophobicity of hydrophobic barrier 118 to help in repelling fluid 120. The opening 122 permits singlet oxygen to escape. In one embodiment, the guard posts 114 are manufactured by printing new rows of elongated posts either before, or after the sensitizer laden elongated posts are fully cured. The as-printed posts are then coated with particles (for example, hydrophobic silica nanoparticles) using processes described for sensitizer particles described elsewhere in this specification.

Thickness of supporting substrate is selected to be sufficiently stiff so that it can be inserted into a pocket of a biological tissue, thin enough to fit into the pocket without exerting too much pressure on the patient and thick enough to make alignment between the substrate and the light source easy to make and reliable to maintain. In one embodiment the elongated posts have a base diameter of about 400 microns, a height of 900 microns and a concave profile. In some embodiments, the use of smaller diameter and shorter posts is advantageous as that would allow more posts to be in or near the pocket.

Figure 4:
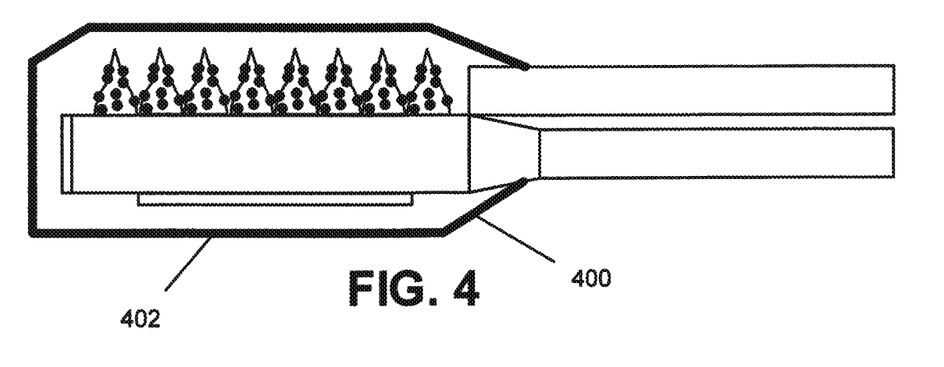
FIG. 4 is a bisected profile view of another assembly that is sealed within a semi-permeable membrane.

FIG. 4 depicts one embodiment that uses a different hydrophobic barrier to protect the sensitizer from surrounding liquids. In the embodiment of FIG. 4, the hydrophobic barrier is semi-permeable membrane 400 that includes opening 402 in the form of pores. Due to the inclusion of semi-permeable membrane 400 the embodiment of FIG. 4 omits guard posts. Singlet oxygen can pass through the semi-permeable membrane 400 but liquids cannot pass through the membrane. Semi-permeable membranes include thin membranes with pore diameters of about 0.05 microns. Pores of this dimension in a hydrophobic substrate (e.g. polyethylene) exhibit a capillary pressure sufficient high (108 psi) to exclude water under all physiologically relevant conditions. Examples include ultrahigh molecular weight polyethylene (UPE) with 0.05 micron pores with a nominal pore area of 85% sold under the tradename SUREVENT®. Some embodiments, not shown, include both a semi-permeable membrane (e.g. semi-permeable membrane 400) and inert particles (e.g. inert particles 112).

Figure 5A:
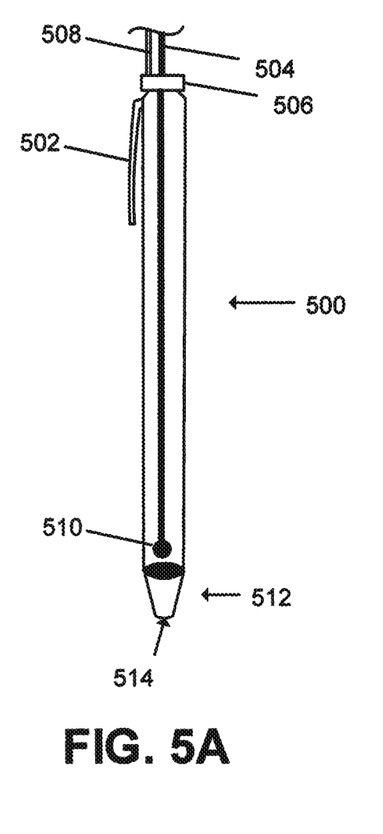
FIG. 5A depicts a hand-piece that generates singlet oxygen using a conical tip.

FIG. 5A depicts a pen-like hand-piece 500 that provides a mechanical separation of the sensitizer from the biofluid. A pen-like hand-piece is a cylindrical hand-piece with a length to width ratio of at least 5:1. In one embodiment, the ratio is at least 10:1. Switches 502 allow the user to control the actualization of light from the optical fiber 504. Oxygen flow control 506 controls the rate of flow of oxygen from oxygen supply tube 508. Light from the optical fiber 504 is routed to a lens 510 that can diffuse light over a wide area within the conical tip 512. The conical tip 512 comprises the sensitizer and elongated posts as described elsewhere in this specification. Outlet 514 emits the newly formed singlet oxygen and any residual triplet oxygen. The lifetime of singlet oxygen in the gas phase is known to be about 1 ms and about 4 µs in aqueous media." An outlet with a 1 mm diameter and a gas flow rate of 0.5 liters per minute causes the gas to flow through the outlet with a velocity of about 8 micro-Liters per ms. Thus singlet oxygen can be generated in the conical tip 512 and conveyed several millimeters before it decays to the ground (inactive) triplet state. The conical tip is removable to facilitate its use as a disposable tip. This permits tips to be used individually for each particular patient to prevent cross-contamination between patients.

Figure 5B:
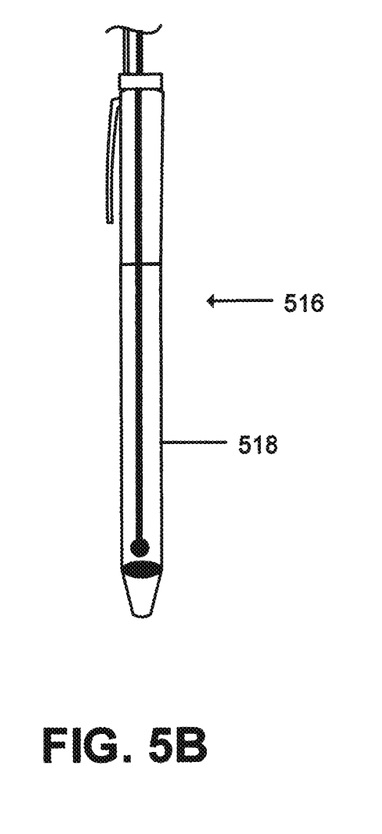
FIG. 5B depicts a catheter that generates singlet oxygen using a conical tip.

FIG. 5B depict a catheter 516. The catheter 516 comprises a disposable sheath 518 that is a relatively stiff support that provides a low-friction exterior. The disposable sheath 518 is sufficiently flexible that it can be pushed into the body. Catheter 516 may have a length to width ratio of at least 10:1. In one embodiment, the ratio is at least 20:1. Examples of catheters including urinary catheters, venous catheters, strength catheters, and the like.

Figure 6:
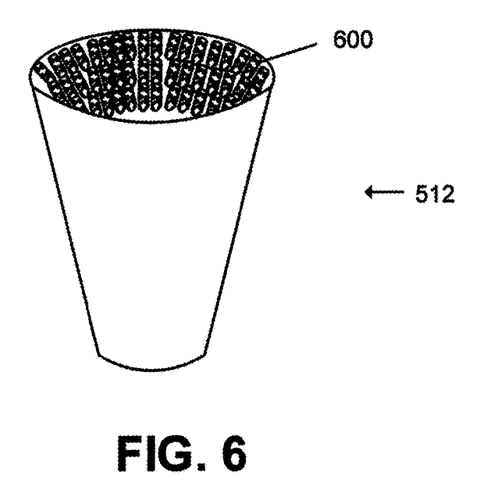
FIG. 6 is a magnified view of a conical tip.

FIG. 6 is a magnified view of an exemplary conical tip 512. The conical tip 512 has a hollow interior whose internal surface is coated with elongated posts 600 which are substantially identical to elongated posts 104. The conical tip 512 may be produced using, for example, the method of FIG. 7.

Figure 7:
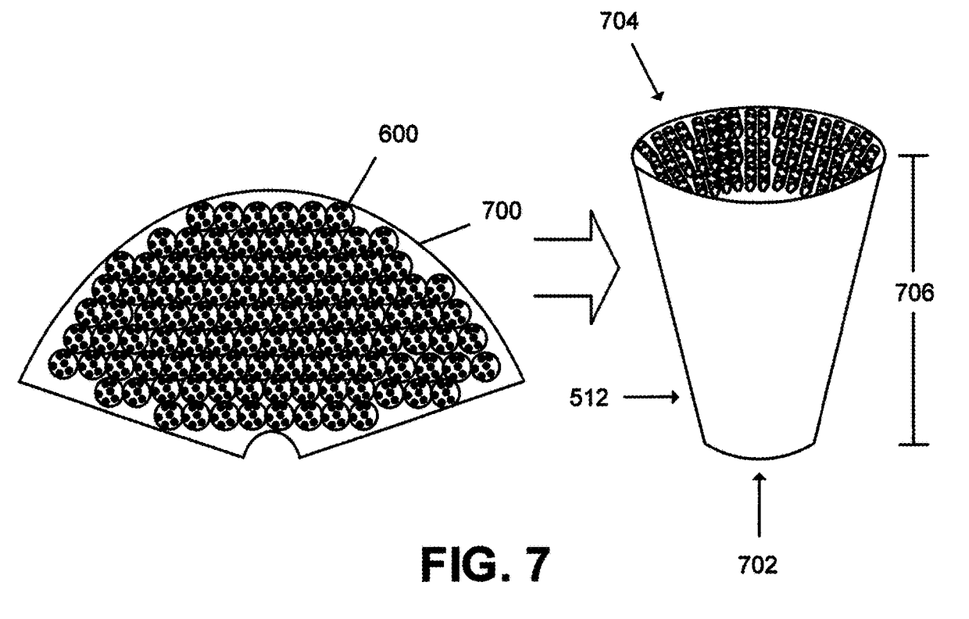
FIG. 7 depicts one method for forming a conical tip.

In FIG. 7, a plurality of elongated posts 600 are applied to a flexible substrate 700. After the sensitizer is applied and the posts 600 are cured the flexible substrate 700 (which is non-permeable) is bent into the conical shape of conical tip 512. The conical tip 512 has a narrow end 702, a wide end 704 and a length 706. In one embodiment, the narrow end 702 has a diameter of about 1 mm, the wide end 704 has a diameter greater than 1 mm but less than 20 mm. The length 706 may be, for example, about 10 mm long.

Figure 8A:
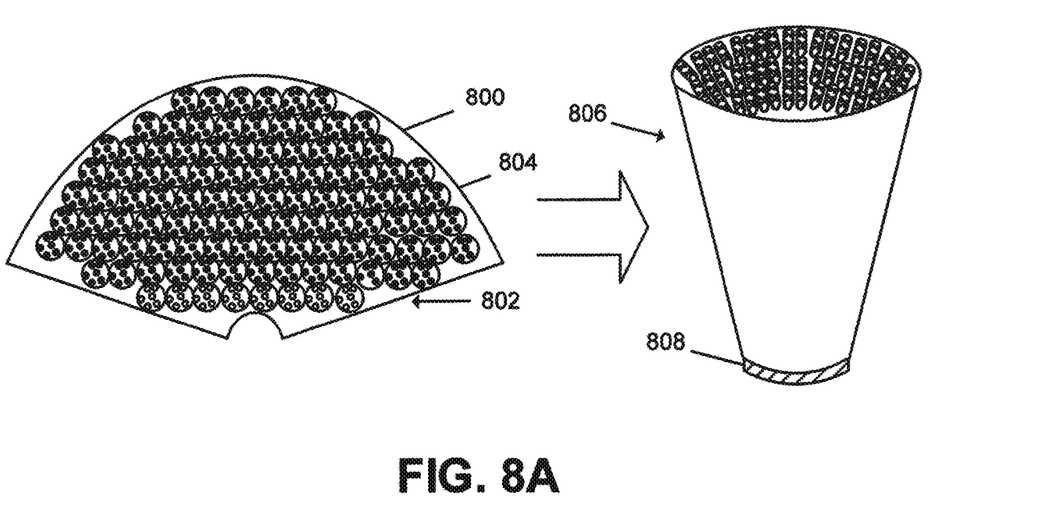
FIG. 8A and FIG. 8B depict two alternative methods for forming a conical tip.

FIG. 8A depicts another method for forming a conical tip 806. A flexible substrate 800 is produced that has both elongated posts 804 with sensitizers and at least one row of guard posts 802. After the sensitizer is applied and the posts 804 are cured the flexible substrate 800 is bent into the conical shape of conical tip 806. A semi-permeable membrane 808 is used to seal the narrow outlet at the narrow end of the conical tip 806. The semi-permeable membrane 808, in combination with the guard posts 802 further protect the elongated posts 804 from contact with biofluids.

Figure 8B:
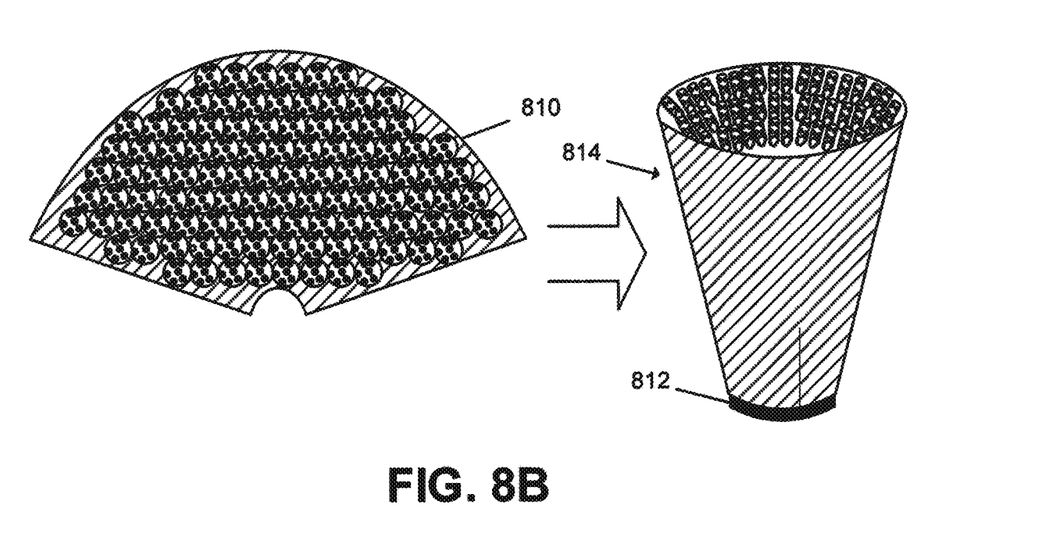

FIG. 8B is similar to FIG. 8A except in that the row of guard posts 802 are omitted, the substrate 810 is a semi-permeable substrate and a non-permeable sealant 812 is used to seal the narrow end of the conical tip 814. The sealant minimizes downward flow of oxygen and promotes the flow of oxygen out of the sides of the conical tip 814 through substrate 810.

Figure 8C:
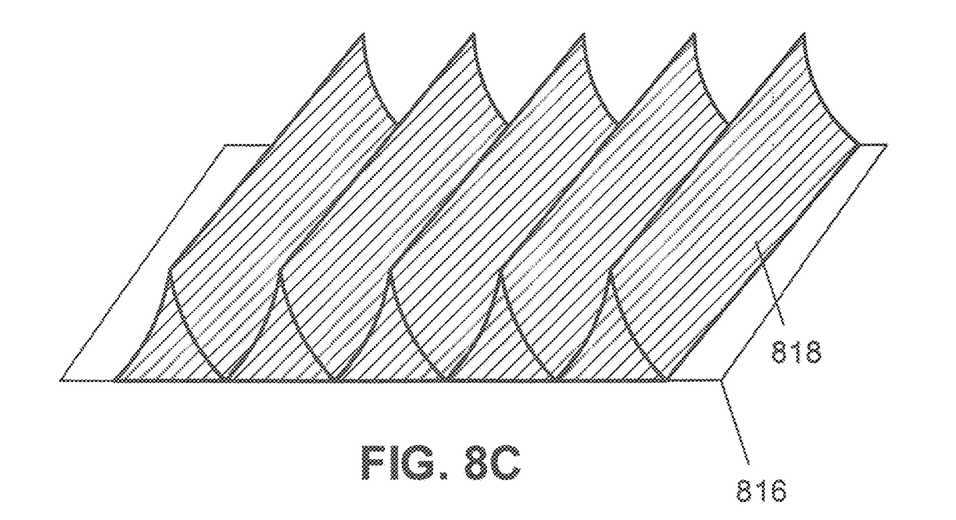
Figure 8D:
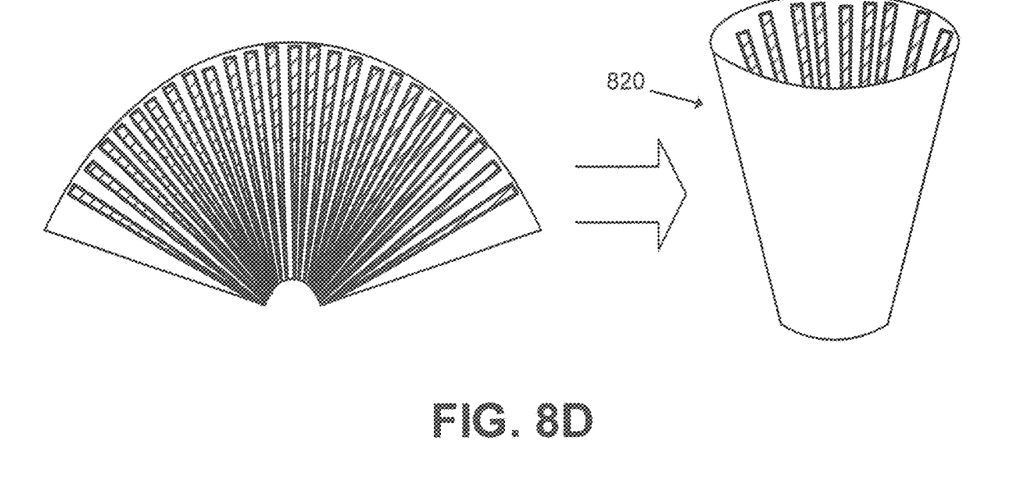
FIG. 8D depicts a method of forming a conical tip and FIG. 9 depicts another method for forming a conical tip.

FIG. 8C depicts an alternative method for forming a hydrophobic barrier. In the embodiment of FIG. 8C the substrate 816 comprises a plurality of elongated ridges 818. Sensitizer can be added to the elongated ridges 818. The elongated ridges 818 define trenches that guide singlet oxygen along the longitudinal axis of the trench. When these trenches are bent into a conical tip 820 (see FIG. 8D) the singlet oxygen is guided toward the outlet of the conical tip.

Figure 9:
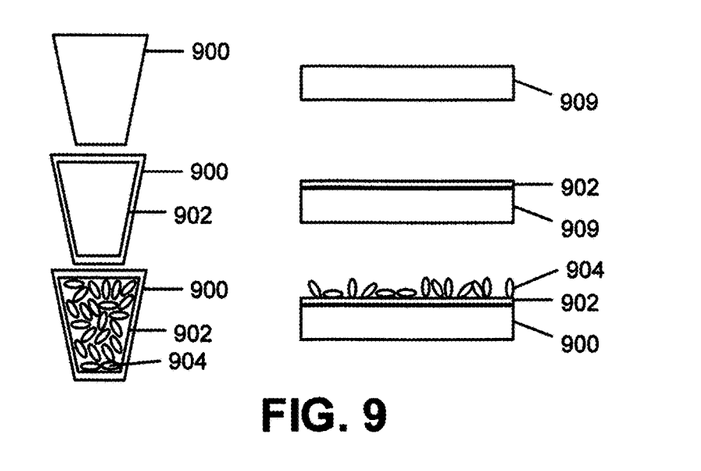

FIG. 9 depicts another method for forming a conical tip. A flexible substrate 900 is coated with a layer of polymeric material 902. Particles 904 with sensitizer disposed thereon are disposed on the layer of polymeric material 902. The polymeric material is then cured. Because the embodiment of FIG. 9 uses particles 904 rather than elongated posts, the use of a semi-permeable membrane is desirable to keep biofluids from contacting the sensitizer. The available surface area is also reduced (relative to the elongated post embodiment). However, the embodiment of FIG. 9 has other advantages, including cost effectiveness.

Figure 10:
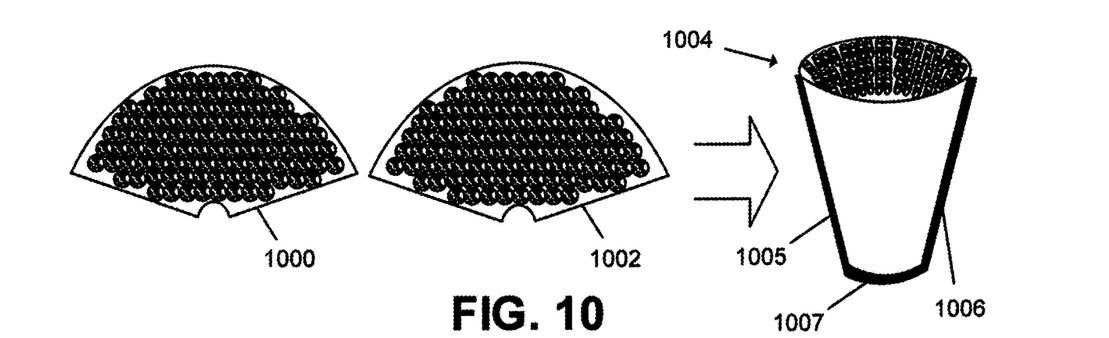
FIG. 10 and FIG. 11 depict two alternative methods for forming a conical tip.

FIG. 10 depicts another method for forming a conical tip. A flexible substrate 1000 (which is a semi-permeable substrate) is coated with sensitizer-containing elongated posts. Likewise a flexible substrate 1002 (which is a non-permeable substrate) is also coated with sensitizer-containing elongated posts. Both of these substrates are bonded together along two long seams 1005 and 1006 as well as along the bottom seam 1007 and bent into a conical shape to form the conical tip 1004. This tip directs the flow of singlet oxygen through only one side of the tip, namely the porous substrate 1000. In this way singlet oxygen would preferentially treat one side of the perio pocket, for example the side facing the tooth, and avoid reacting with the opposite side, for example the side facing the gum. The bonding of 1000 and 1002 can be accomplished with an adhesive, such as PDMS. Alternatively, the two substrates 1000 and 1002 could be heat sealed or ultrasonically sealed if the substrates are fabricated using a thermoplastic substrate such as polyethylene or polyvinylidene fluoride.

Figure 11:
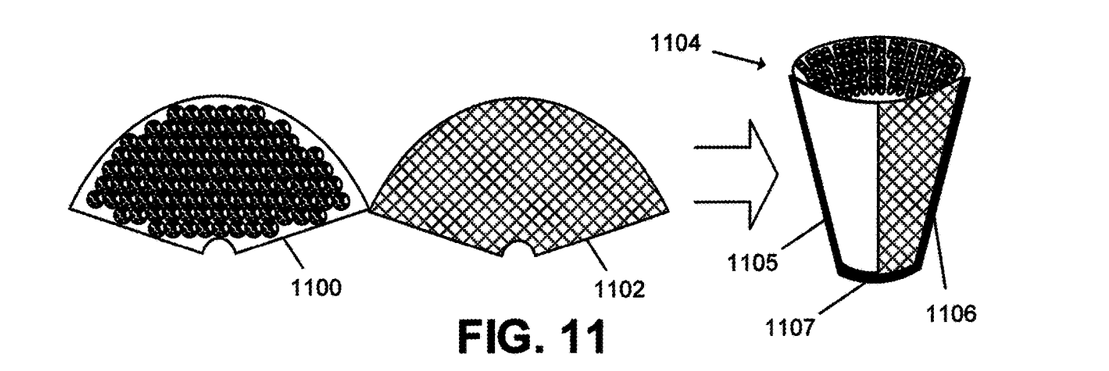

FIG. 11 depicts another method for forming a conical tip. A flexible substrate 1100 (which is a semi-permeable substrate) is coated with sensitizer-containing elongated posts. An optically reflective substrate 1102 is also provided which is flexible. The optically reflective substrate can be a thin metal reflective foil, such as aluminum foil which is approximately 25 microns thick, or it can be a metallized plastic substrate such as vapor deposited aluminum on polyester (Trade Name MYLAR®) where the aluminum thickness is less than 1 micron and the MYLAR® thickness is in the range of 12-150 microns. The two substrates are bonded together to form seams 1105, 1106 and 1107 along the two sides and bottom and bent into a conical shape to form the conical tip 1104. As described elsewhere in this specification, this tip directs the flow of singlet oxygen through only one side of the tip, namely the porous substrate 1100. The reflective substrate 1102 increases the light impinging on sensitizers supported on substrate 1100 and so will increase the quantity of singlet oxygen generated by the device and compensate, in part, for the lower total surface area of sensitizer as compared to, for example, the tip described in FIG. 7. In some embodiments, a second light source is incorporated to provide a second wavelength of light (for the purpose of photobiomodulation) that is reflected off the optically reflective substrate 1102 and exits the conical tip 1104 along with the oxygen. The second wavelength of light may be chosen so that it is not absorbed by the sensitizer thereby increasing the amount of light transmitted as well as preventing heating of the sensitizer which can hasten sensitizer degradation. The substrate 1100 should be chosen so that it does not absorb the second wavelength. The second wavelength is typically in the visible portion of the spectrum and so substrate 1100 could be composed of optically transparent polymers. Many such polymers exist and two examples include polyvinylidene fluoride and polyethylene. The substrate 1100 may appear white due to scattering of light from the rough surface texture and, in some cases, polymer crystals formed in the film. Some light may be scattered back into the tip whereas other light will be scattered in the forward direction and into the tissues of the perio pocket.

Figure 12:
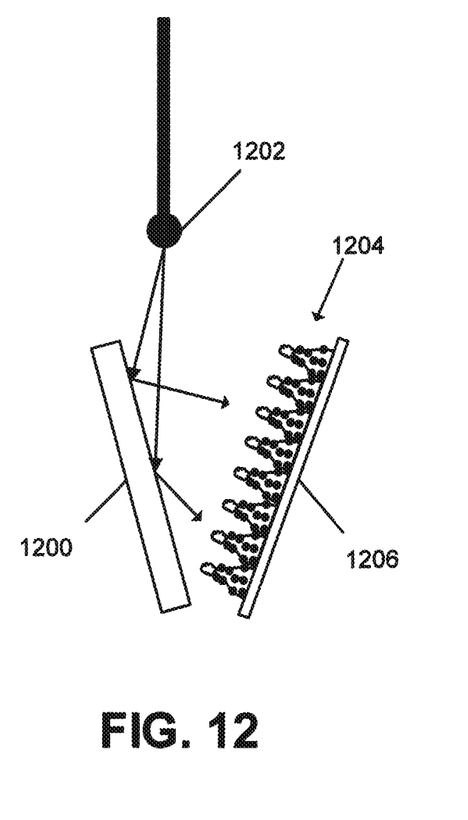
FIG. 12 depicts the use of a reflective substrate to redirect light to promote the generation of singlet oxygen.

FIG. 12 depicts the use of a reflective substrate 1200 to redirect light from a lens 1202 to a plurality of elongated posts 1204. In the embodiment of FIG. 12, the elongated posts 1204 are disposed on a semi-permeable substrate 1206. The substrate can be a reflective metal surface such as aluminum or stainless steel. Alternatively, the reflective substrate could have a thin layer of a reflective metal such as aluminum or silver deposited onto a rigid substrate such as glass or a flexible substrate such as polyester.

Figure 13:
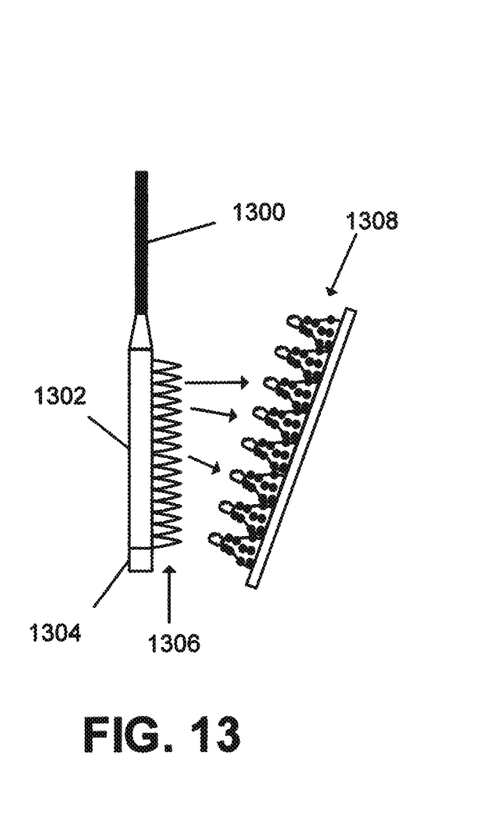
FIG. 13 depicts the use of Frustrated Total Internal Reflection to promote the generation of singlet oxygen.

FIG. 13 depicts an optical fiber 1300 that provides light to a transparent substrate 1302. Transmitted light is reflected by a mirror 1304 to maximize optical efficiency. An array of optically transparent protrusions 1306 are provided to construct a system for Frustrated Total Internal Reflection. This enhances the amount of light that is provided to elongated posts 1308.

Figure 14A:
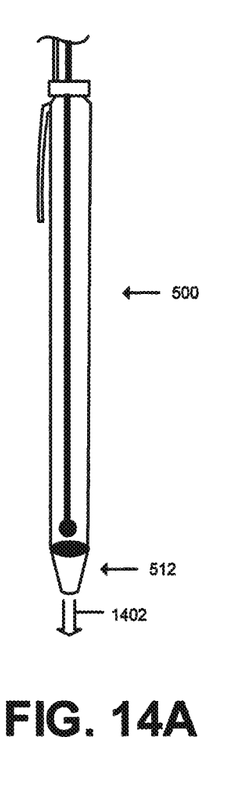
FIG. 14A to FIG. 14D depict a variety of hand-pieces with a variety of conical tips.
Figures 14B, 14C, 14D:
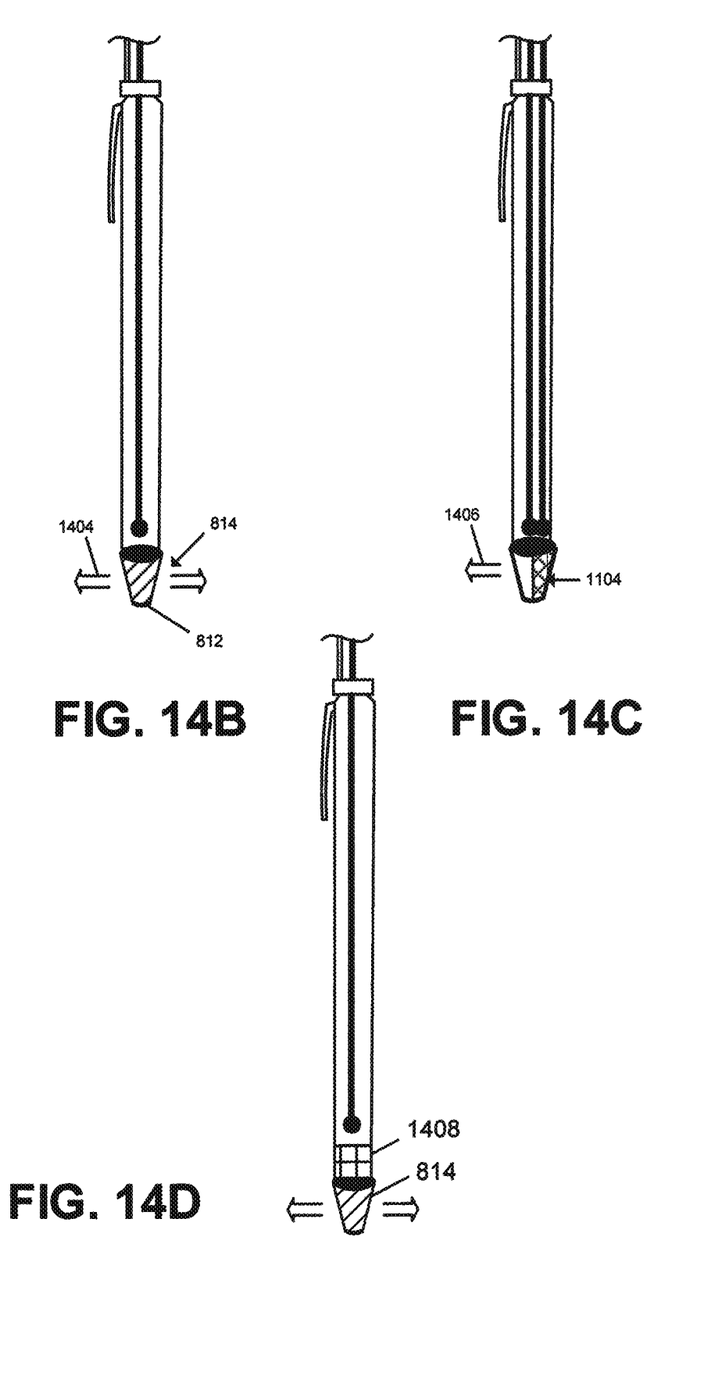

FIG. 14A to FIG. 14D depict various pen-like handpieces. FIG. 14A depicts the hand-piece 500 described elsewhere in this specification. The sides of the conical tip 502 are a non-permeable membrane while the narrow end is open. This promotes oxygen flow along downward arrow 1402. FIG. 14B uses the conical tip 814 with a non-permeable sealant 812. The sides of the conical tip 814 is a permeable membrane while the narrow end is closed. This promotes oxygen flow along sideways arrows 1404. FIG. 14C uses the conical tip 1104 with the flexible substrate 1100 (which is porous) and one the optically reflective substrate 1102 (which is non-permeable). This promotes oxygen flow along sideways arrow 1406 through porous surface 1100. FIG. 14D uses a porous glass tip 1408 along the light path. The porous glass tip 1408 is depicted in further detail in FIG. 15A to FIG. 15D. The oxygen flows through the porous glass and exits the end of hand-piece 500 in any direction that has not been sealed to exclude gas flow.

Figure 15A:
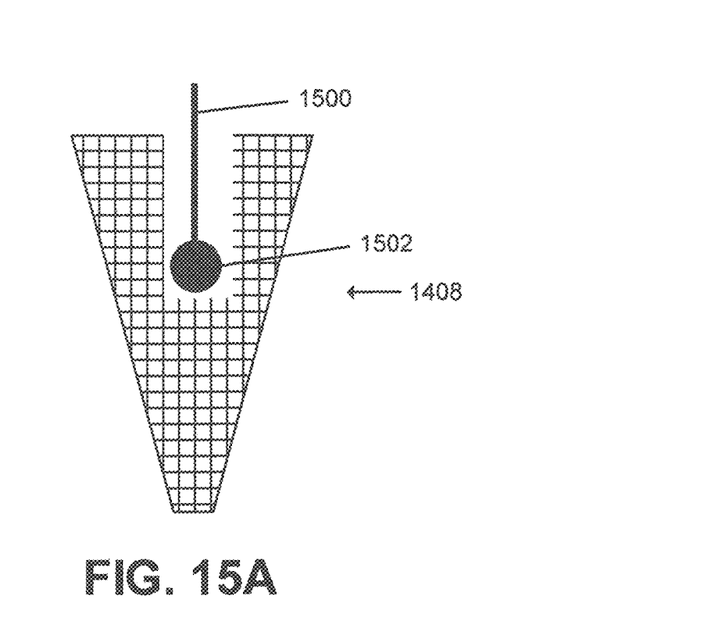
FIG. 15A to FIG. 15D depicts the use of porous glass tip to promote the generation of singlet oxygen.
Figure 15B:
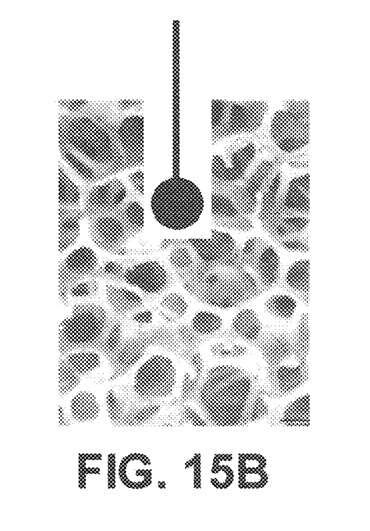
Figure 15C:
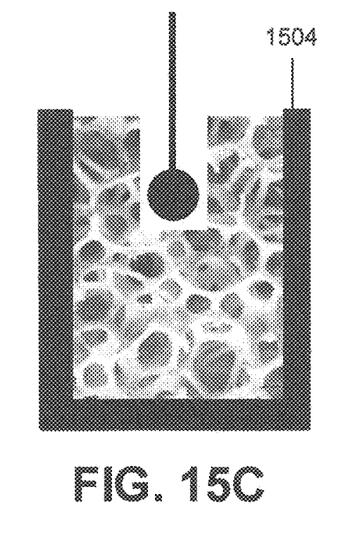
Figure 15D:
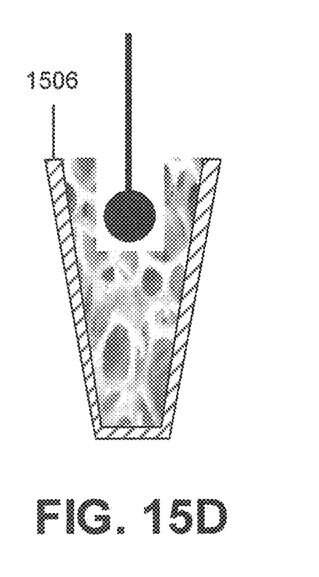

FIG. 15A depicts the porous glass 1408. An optical fiber 1500 routes light to lens 1502 that functions as a coupler to spread light through the porous glass 1408. The porous glass 1408 is embedded/infiltrated with sensitizer. FIG. 15B is an optical image showing the porosity of porous glass. In one embodiment, the porous support comprises a variety of materials including glass, alumina ($Al_2O_3$), other ceramics, or polymers such a polyvinylidene fluoride or polyethylene. In FIG. 15C the surface 1504 of the porous glass is treated to be superhydrophobic. The pores are sufficiently small (e.g. less than 1 micron diameter) to keep water/biofluids from contacting the sensitizer. In one embodiment, the glass surface is treated with fluorosilane to render it superhydrophobic. In another embodiment, the glass surface is coated with PDMS and coated with silica nanoparticles. In another embodiment, the glass surface is treated with a chlorosilane or an alkoxysilane to render it superhydrophobic. In another embodiment, the glass surface is coated with a thin layer of a siloxane polymer such as PDMS. In another embodiment, the glass surface is coated with a thin fluoropolymer by using a commercially available fluoropolymer solution such as TEFLON® AF or Cytop. FIG. 15D shows a semi-permeable membrane 1506 that prevents contact between the sensitizer and biofluids while permitting singlet oxygen to escape. The semi-permeable membrane 1506 can be replaced after each use to avoid cross-contamination between patients. The porous glass 1408 can also be removed as needed to avoid cross-contamination and/or to replenish sensitizer as it becomes oxidized.

Figure 16A:
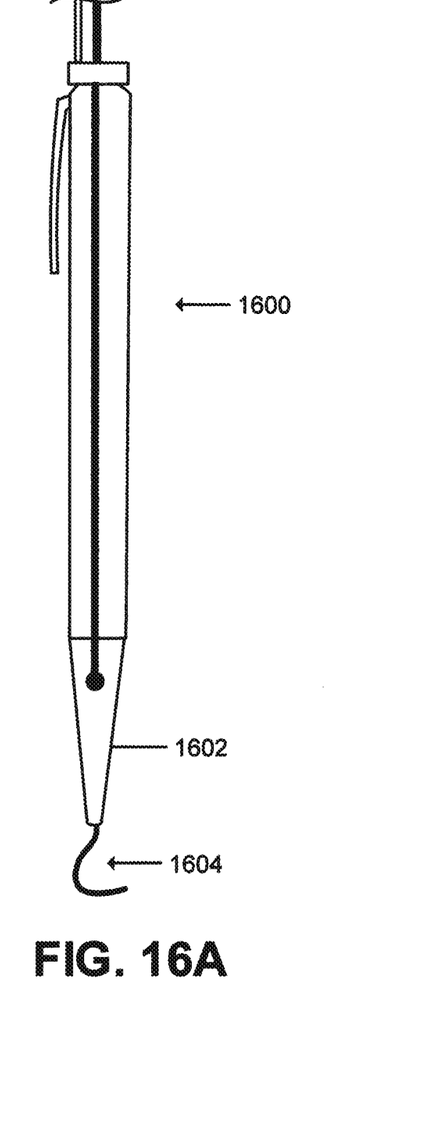
FIG. 16A to FIG. 16C depict a hand-piece that promotes the generation of singlet oxygen wherein the hand-piece uses a variety of scaling tools.
Figure 16B:
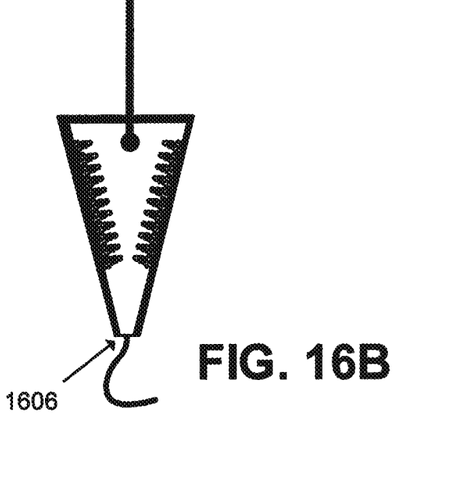
Figure 16C:
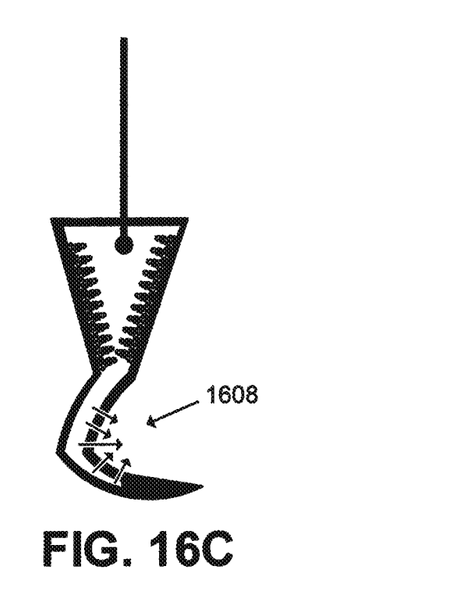

FIG. 16A depicts a combination scaler and PDT device 1600. The conical tip 1602 may be parallel to the scaling tool (not shown) or, as shown in FIG. 16B, the scaling tool 1604 may emanate from the narrow end of the conical tip 1602. The sides of the conical tip 1602 are non-permeable which directs oxygen downward. In one embodiment (see FIG. 16B), an outlet 1606 is provided at the narrow end of the conical tip 1602 and prior to the scaling tool 1604. Oxygen is emitted through the outlet 1606. In another embodiment (see FIG. 16C), the outlet 1606 is omitted and the scaling tool 1602 is hollow. Oxygen is directed out of outlet 1608 in the tip of scaling tool 1602.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A device for generating singlet oxygen, the device comprising:
 a hand-piece comprising
  a conical tip at a terminus of the hand-piece;
  a gas supply tube that conveys oxygen to the conical tip;
  an optical fiber that conveys light to the conical tip;
  wherein the conical tip is detachable from the hand-piece and comprises:

a cylindrical substrate with an internal surface that is at least partially coated with particles that comprise a sensitizer, wherein the sensitizer converts triplet oxygen to singlet oxygen upon exposure to light;

the optical fiber conveys light to the sensitizer;

the gas supply tube is disposed upstream of the sensitizer such that oxygen is conveyed to the sensitizer;

at least one opening disposed downstream of the sensitizer that directs singlet oxygen to a treatment site;

a hydrophobic barrier that separates the sensitizer particles from the at least one opening, thereby protecting the sensitizer from contacting an external fluid.

2. The device as recited in claim 1, wherein the hydrophobic barrier comprises a semi-permeable membrane.

3. The device as recited in claim 1, wherein the hydrophobic barrier comprises a semi-permeable membrane wherein the semi-permeable membrane has pores with a diameter of between 0.4 nm and 1,000 nm.

4. The device as recited in claim 1, wherein the particles are between 10 microns and 100 microns in diameter.

5. The device as recited in claim 1, wherein the particles are between 1 nm and 10 microns in diameter.

6. The device as recited in claim 1, wherein the particles are between 1 nm and 500 nm in diameter.

7. The device as recited in claim 1, wherein the particles are comprised of a second material whose composition is different than a composition of the sensitizer and the particles are between 1 micron and 500 microns in diameter.

8. The device as recited in claim 7, wherein the second material is glass.

9. The device as recited in claim 7, wherein the sensitizer is a silicon-phthalocyanine and the second material is a sol-gel material.

10. The device as recited in claim 1, where the hand-piece has a length to width ratio of at least 5:1.

11. The device as recited in claim 1, wherein the optical fiber that conveys light to the conical tip in configured to convey a light having a first wavelength, the device further comprising a second optical fiber that conveys light having a second wavelength to the conical tip, wherein the sensitizer does not absorb the second wavelength.

12. The device as recited in claim 1, wherein the cylindrical substrate is optically transparent.

13. The device as recited in claim 1, further comprising a disposable sheath between the hand-piece and the conical tip, wherein the device has a length to width ratio of at least 10:1.

14. The device recited in claim 1 wherein the hydrophobic barrier is comprised of a plurality of elongated posts extending from the internal surface of the cylindrical substrate, each elongated post comprising the particles.

15. The device as recited in claim 14, wherein the hydrophobic barrier provides a superhydrophobic surface.

16. The device recited in claim 14, wherein each elongated post has a top and the tops of the elongated posts are coated with inert hydrophobic particles.

17. The device recited in claim 14 wherein the elongated posts are circumscribed with a plurality of guard posts, each guard post being coated with inert hydrophobic particles.

18. The device as recited in claim 14, wherein the elongated posts comprise polydimethylsiloxane (PDMS) and the particles are coated onto the lateral sides of the PDMS.

19. The device recited in claim 1 wherein the hydrophobic barrier is comprised of a plurality of elongated ridges extending from the internal surface of the cylindrical substrate, each elongated ridge comprising the particles.

20. A method for treating a periodontal pocket of a patient with singlet oxygen, the method comprising:

conveying a gas comprising triplet oxygen through a hand-piece, the hand-piece comprising a conical tip at a terminus of the hand-piece;

a gas supply tube that conveys oxygen to the conical tip;

an optical fiber that conveys light to the conical tip;

wherein the conical tip is detachable from the hand-piece and comprises:

a cylindrical substrate with an internal surface that is at least partially coated with particles that comprise a sensitizer, wherein the sensitizer converts the triplet oxygen to singlet oxygen upon exposure to light;

the optical fiber conveys light to the sensitizer;

the gas supply tube is disposed upstream of the sensitizer such that oxygen is conveyed to the sensitizer;

at least one opening disposed downstream of the sensitizer that directs singlet oxygen to a treatment site;

a hydrophobic barrier that separates the sensitizer particles from the at least one opening, thereby protecting the sensitizer from contacting an external fluid.

inserting the at least one opening of the conical tip into the periodontal pocket of the patient such that the at least one opening is proximate the treatment site;

actuating a light source that provides light to the optical fiber, thereby converting the triplet oxygen to the singlet oxygen using the sensitizer;

permitting the singlet oxygen to flow from the sensitizer to the at least one opening and then to the treatment site, thereby treating the periodontal pocket of the patient with the singlet oxygen.

\* \* \* \* \*

UNITED STATES PATENT AND TRADEMARK OFFICE
CERTIFICATE OF CORRECTION

| | |
|---|---|
| PATENT NO. | : 10,835,629 B2 |
| APPLICATION NO. | : 15/729005 |
| DATED | : November 17, 2020 |
| INVENTOR(S) | : Alan M. Lyons, Alexander Greer and QianFeng Xu |

It is certified that error appears in the above-identified patent and that said Letters Patent is hereby corrected as shown below:

In the Specification

Column 1, after Line 11, insert the following text:
--STATEMENT OF FEDERALLY SPONSORED RESEARCH OR DEVELOPMENT
This invention was made with Government support under grant number 1R41DE026083-01A1 awarded by the National Institute of Health. The government has certain rights in the invention.--

Signed and Sealed this
Ninth Day of July, 2024

Katherine Kelly Vidal
*Director of the United States Patent and Trademark Office*